US00PP37274P3

(12) United States Plant Patent
Wilde

(10) Patent No.: US PP37,274 P3
(45) Date of Patent: Feb. 17, 2026

(54) ***ILEX* PLANT NAMED 'MONWILDE'**

(50) Latin Name: *Ilex meserveae*
Varietal Denomination: MONWILDE

(71) Applicant: Jeffrey H Wilde, Cincinnati, OH (US)

(72) Inventor: Jim Wilde, Cincinnati, OH (US)

(73) Assignee: Monrovia Nursery Company Inc., Azusa, CA (US)

( * ) Notice: Subject to any disclaimer, the term of this patent is extended or adjusted under 35 U.S.C. 154(b) by 0 days.

(21) Appl. No.: 18/762,341

(22) Filed: Jul. 2, 2024

(65) Prior Publication Data

US 2026/0013408 P1 Jan. 8, 2026

(51) Int. Cl.
*A01H 6/00* (2018.01)
*A01H 5/02* (2018.01)

(52) U.S. Cl.
USPC ..... Plt./247

(58) Field of Classification Search
USPC ..... Plt./247
CPC ..... A01H 6/00; A01H 5/02
See application file for complete search history.

*Primary Examiner* — Keith O. Robinson

(57) ABSTRACT

A new and distinct variety of *Ilex* plant named 'MONWILDE' is disclosed, characterized by a true dwarf plant habit. Plants of 'MONWILDE' have been observed to have a mature size of three to four feet tall and three to four feet wide. The new variety grows into a compact, rounded form. Abundant berry set can occur from Fall through Winter, with a compatible male pollinizer present. The new cultivar is a *Ilex*, suitable for horticultural purposes.

2 Drawing Sheets

Latin name of the genus and species: *Ilex meserveae*.
Variety denomination: 'MONWILDE'.

BACKGROUND OF THE INVENTION

The new cultivar, hereinafter referred to as 'MONWILDE', was discovered as a single seedling plant growing in a field of the commercial varieties *Ilex*, 'Mesid' U.S. Plant Pat. No. 4,685 and *Ilex* (Holly) Plant, U.S. Plant Pat. No. 2,434. Both of these varieties are presumed to be a parent. As the new cultivar was selected as a field seedling, the inventor cannot identify which parent variety is the seed parent and which is the pollen parent. The inventor selected the new variety at a commercial nursery in Cincinnati, OH in the Summer of 2015.

The inventor first asexually propagated 'MONWILDE' by semi-softwood cuttings at the same commercial nursery during the Fall of 2015. The inventor continued controlled testing and propagation, assessing stability of the unique characteristics of this variety. At least six generations have been reproduced and have shown that the unique features of this cultivar are stable and reproduced true to type.

SUMMARY OF THE INVENTION

The cultivar 'MONWILDE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONWILDE'. These characteristics in combination distinguish 'MONWILDE' as a new and distinct *Ilex* cultivar:

1. Female holly with a true dwarf habit, reaching 3 to 4 feet tall and 3 to 4 feet wide at maturity.

2. Compact, rounded form.
3. Abundant berry set from fall through winter, provided there is a compatible male pollinizer.

COMPARISON TO PARENT VARIETIES

*Ilex* 'MONWILDE' differs from *Ilex meserveae* 'Mesid' in the following:

1. The new variety is a dwarf, reaching 3 to 4 feet tall and 3 to 4 feet wide at maturity; 'Mesid' reaches 8 to 10 feet tall and 6 to 8 feet wide at maturity.
2. The new variety has a naturally compact and rounded form; 'Mesid' has a distinctive pyramidal natural form.
3. The new variety has green foliage; Mesid' has dark green foliage.

*Ilex* 'MONWILDE' differs from *Ilex meserveae* (Holly) Plant, U.S. Plant Pat. No. 2,434 in the following:

1. The new variety is a dwarf, reaching 3 to 4 feet tall and 3 to 4 feet wide at maturity; (Holly) Plant, U.S. Plant Pat. No. 2,434 reaches 6 to 8 feet tall and 3 to 6 feet wide at maturity.
2. The new variety has a naturally compact and rounded form; (Holly) Plant, U.S. Plant Pat. No. 2,434 has a dense upright form.
3. The new variety has green foliage; (Holly) Plant, U.S. Plant Pat. No. 2,434 has blue-green foliage.

COMMERCIAL COMPARISON

*Ilex* 'MONWILDE' can be compared to the commercial variety of *Ilex meserveae* 'Blue Princess', U.S. Plant Pat. No. 3,675. Plants are similar in most horticultural characteristics; however, plants of the new variety differ in the following:

1. The new variety is a dwarf, reaching 3 to 4 feet tall and 3 to 4 feet wide at maturity; 'Blue Princess' grows to 8 to 10 feet tall and 6 to 8 feet wide at maturity.
2. The new variety has a naturally compact and rounded form; 'Blue Princess' has a more broader, more spreading form.

*Ilex* 'MONWILDE' can be compared to the unnamed commercial variety *Ilex meserveae* 'Mondo', U.S. Plant Pat. No. 9,999. Plants are similar in most horticultural characteristics; however, plants of the new variety differ in the following:

1. The new variety is a female holly and will produce berries; 'Mondo' is a male holly and will not produce berries.
2. The new variety grows 3 to 4 feet tall and 3 to 4 feet wide at maturity; 'Mondo' grows to 2 feet tall and 3 feet wide at maturity.
3. The new variety has glossy green foliage and produces red berries in the fall; 'Mondo' has dark green glossy foliage with burgundy hues and turns deep purple in the winter, and does not produce berries.
4. The new variety is female and produces red berries in the fall with a compatible pollinizer; 'Mondo' does not produce berries but can act as a pollinizer for female blue hollies.

BRIEF DESCRIPTION OF THE PHOTOGRAPHS

The accompanying photographs illustrate in full color a typical plant of 'MONWILDE' grown outdoors in Dayton, OR.

Figure 1:
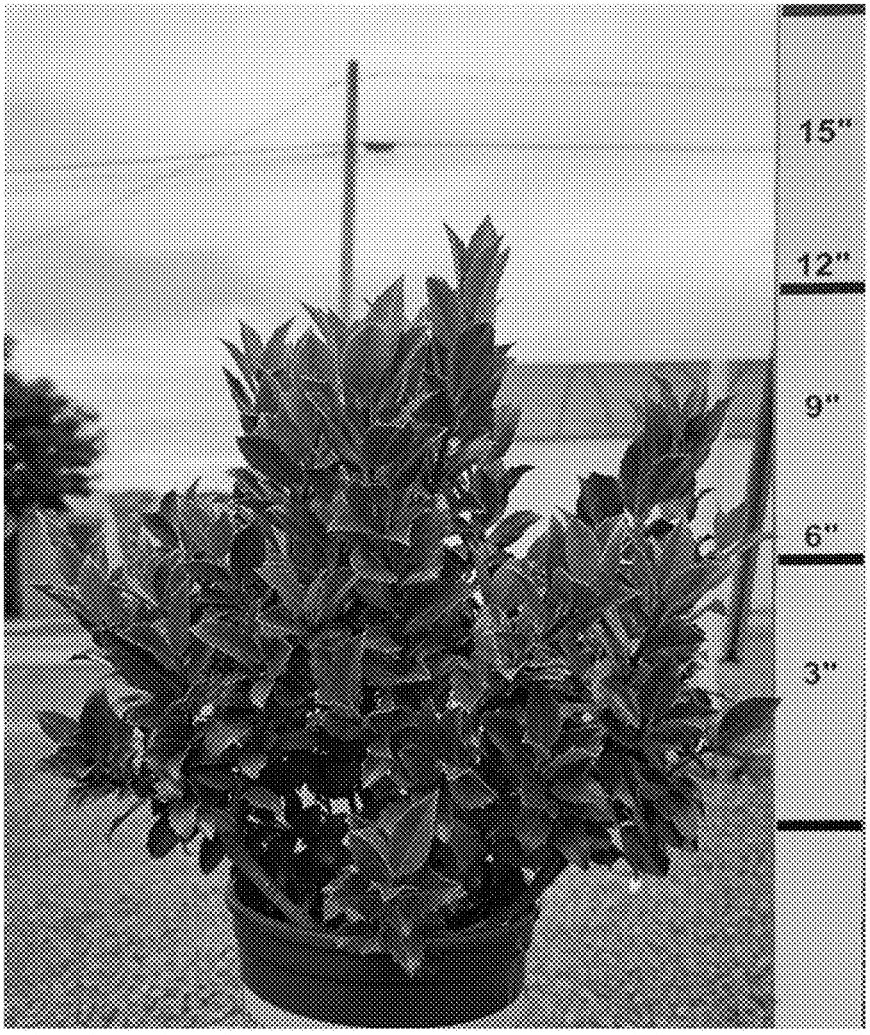
FIG. 1 is a plant of approximately 1 year old, in a 1-gallon pot.
Figure 2:
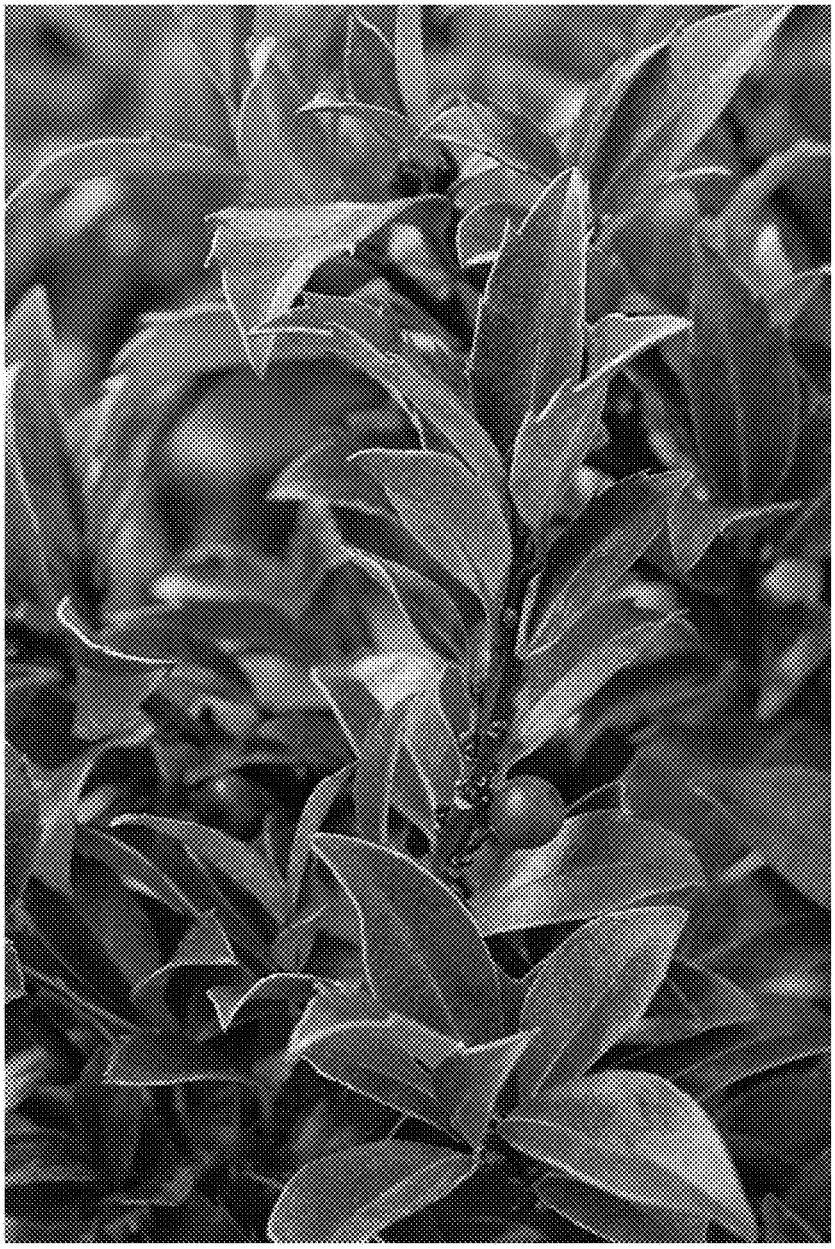
FIG. 2 illustrates foliage and a typical berry from the new variety.

Photos were taken during the Spring and illustrate new growth and young foliage. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONWILDE' plants grown outdoors in Dayton, OR. Plants are approximately 1 year old, in a 1-gallon nursery container. Measurements and numerical values represent averages of typical plant types.

Botanical classification: *Ilex meserveae* 'MONWILDE'.

PROPAGATION

Typically by semi-hardwood cuttings in Spring and Summer.

Root description: Semi-woody, moderately dense roots. Colored near RHS Grey-Brown 199A.

PLANT

Growth habit: Compact, rounded

Height: Approximately 40 cm.

Plant spread: Approximately 35 cm.

Branching characteristics: 4 to 6 main branches from pinch, emerging at 30 to 45 degrees from center.

Length of main branches: Average range 12 cm to 21 cm. Diameter of Main Branches: 9 to 11 mm.

Lateral branches: Each main branches has an average range of 8 to 12 lateral branches occurring at approximately 45° from main branch. Alternate.

Diameter of lateral branches: Approximately 4 mm.

Pinching required:

*Details of pinching.*—Pinch given early at base of plant to encourage more branching.

Branch shape: Round.

Branch strength: Strong, flexible.

Branch color: Oldest growth near RHS Green 137B. New growth near Greyed-Purple 187A.

Branch texture: New growth smooth. Oldest growth smooth with lenticels.

*Lenticels.*—Irregular occurring. Moderately dense. Somewhat irregular ovate. About 2 to 3 mm long and 1 to 2 m wide. Colored near Grey-Grown 199D.

Internode length: 2 to 4 cm.

FOLIAGE

Leaf:

*Arrangement.*—Alternate.

*Density.*—Dense.

*Average length.*—Approximately 3.5 cm.

*Average width.*—Approximately 2 cm.

*Shape of blade.*—Ovate.

*Apex.*—Acute with moderately sharp tooth.

*Base.*—Broad tapered.

*Attachment.*—Stalked.

*Margin.*—Sparsely toothed. Average 4 teeth per leaf, moderately sharp. Oldest foliage entire.

*Texture of top surface.*—Glabrous.

*Texture of bottom surface.*—Glabrous.

*Appearance of top surface.*—Very glossy.

*Appearance of bottom surface.*—Matte.

*Leaf internode length.*—9 to 15 mm.

*Color.*—Young foliage upper side: Near R.H.S. Green 137A. Young foliage under side: Near R.H.S. Yellow-Green 144B. Mature foliage upper side: Near R.H.S. Green 139A. Mature foliage under side: Near R.H.S. Yellow-Green 144B.

*Venation.*—Type: Pinnate. Venation color upper side: Near R.H.S. Yellow-Green 145D. Venation color under side: Near R.H.S. Yellow-Green 144C.

Petiole:

*Average length.*—Approximately 6 mm.

*Diameter.*—Approximately 2 mm.

*Color.*—Near R.H.S. Yellow-Green 144C flushed Greyed-Orange 165A.

FLOWER

Axillary flowers: Flowering begins around late May to early June.

Flower size:

*Diameter.*—3 mm.

*Depth.*—3 mm.

Peduncle:

*Length.*—2 mm.

*Diameter.*—1 mm.

*Color.*—Near Yellow-Green 144C.

*Texture.*—Glabrous.

Petals:
*Petal arrangement*.—Cruciform.
*Length*.—0.8 mm.
*Width*.—2 mm.
*Shape*.—Orbicular.
*Margin*.—Entire.
*Apex*.—Rounded.
*Base*.—Broad cuneate.
*Petal quantity*.—4.
*Texture*.—Glabrous all surfaces.
*Appearance*.—Matte all surfaces.
*Color*.—When opening: Upper surface: Near RHS Green-White 157D. Lower surface: Near RHS Green-White 157D. Fully opened: Upper surface: Near RHS Green-White 157D. Lower surface: Near RHS Green-White 157D.

Bud:
*Shape*.—Globular.
*Length*.—Approximately 1 mm.
*Diameter*.—Approximately 1 mm.
*Color*.—Near RHS Green-White 157A.

Sepals:
*Quantity*.—4.
*Length*.—0.5 mm.
*Width*.—0.3 mm.
*Shape*.—Deltate.
*Color*.—Interior Surface: Near RHS Yellow-Green 144C. Exterior Surface: Near RHS Yellow-Green 144C.
*Texture*.—All surfaces glabrous.

Fragrance: None detected.

REPRODUCTIVE ORGANS

Gynoecium only:
Pistil:
*Number*.—1 per flower.
*Length*.—Approximately 2 mm.
Style length.—0.5 mm.
*Stigma shape*.—Linear.
*Ovary shape*.—Round.

FRUIT AND SEED

Fruit:
*Type*.—Berry-like drupe.
*Shape*.—Round.
*Length*.—About 7 mm.
*Width*.—About 7 mm.
*Color*.—RHS Red 45B.
*Texture*.—Glabrous.

Seed:
*Number*.—1 to 3 per fruit.
*Length*.—About 2 mm.
*Width*.—About 3 mm.
*Color*.—RHS Brown N200C.
*Texture*.—Glabrous.

OTHER CHARACTERISTICS

Disease and pest resistance: Neither resistance nor susceptibility to normal diseases and pets of *Ilex* observed.

Temperature tolerance: Observed cold tolerant to at least USDA Zone 6.

What is claimed is:

1. A new and distinct cultivar of *Ilex* plant named 'MONWILDE' as herein illustrated and described.

* * * * *